United States Patent [19]

Hale

[11] 4,220,307
[45] Sep. 2, 1980

[54] MEDIAL STOOLS

[76] Inventor: Dean H. Hale, 2424 N. Main St., Logan, Utah 84321

[21] Appl. No.: 10,659

[22] Filed: Feb. 9, 1979

[51] Int. Cl.³ .......................................... F16M 11/00
[52] U.S. Cl. .................................. 248/404; 108/147; 248/162.1; 297/347
[58] Field of Search ............................ 248/162.1, 404; 297/347, 61; 91/4 R; 92/240; 108/147

[56] References Cited

U.S. PATENT DOCUMENTS

| | | | |
|---|---|---|---|
| 3,339,873 | 9/1967 | Hale | 248/404 |
| 3,861,740 | 1/1975 | Tajima et al. | 297/195 |
| 3,920,209 | 11/1975 | Komura | 248/162.1 |
| 4,061,304 | 12/1977 | Schattmaier | 248/404 |

FOREIGN PATENT DOCUMENTS

| | | | |
|---|---|---|---|
| 1365427 | 5/1964 | France | 248/404 |
| 1173916 | 11/1966 | United Kingdom | 248/162.1 |

*Primary Examiner*—James T. McCall
*Attorney, Agent, or Firm*—Lynn G. Foster

[57] ABSTRACT

A medical stool with a seat the vertical location of which may be varied by the user through telescopic extension and retraction of tubular members comprising a post assembly selectively relatively displaced by the weight of the user and pressure from within a tank disposed beneath the stool seat as controlled by a valve assembly situated centrally interior of the tank and manually actuated from time to time as desired using a lever located beneath the seat.

12 Claims, 5 Drawing Figures

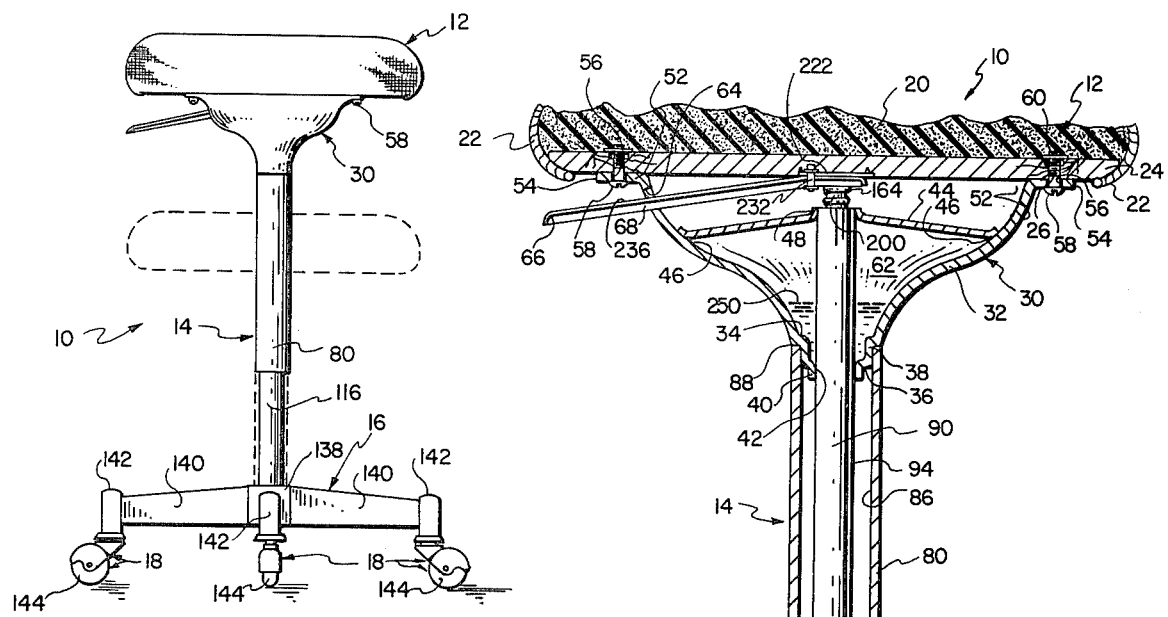
Fig. 1
Fig. 2
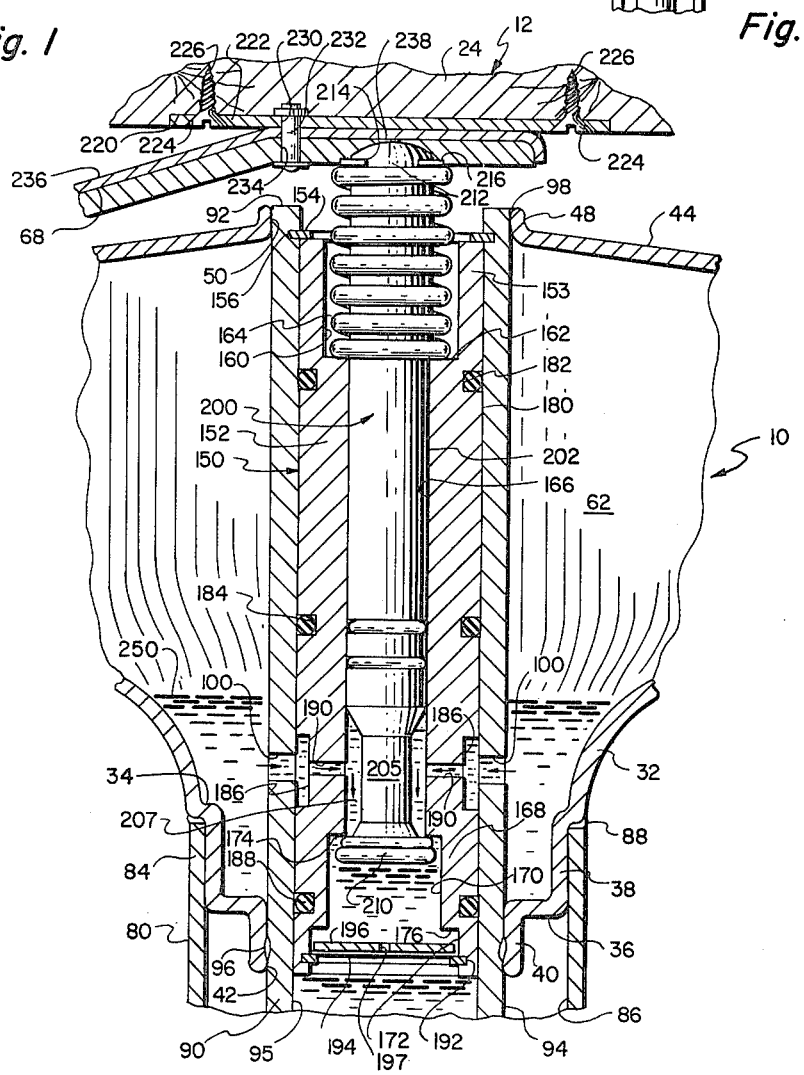
Fig. 3

MEDIAL STOOLS

BACKGROUND

1. Field of Invention

This invention relates generally to stools, and more particularly to a medical stool or the like the cost of which is comparatively low and the operation of which is relatively precise by which the vertical location of the seat of the stool may be varied from time to time as desired by the user.

2. Prior Art

The present invention is an improvement of substantial significance over the subject matter of my prior U.S. Pat. Nos. 3,339,873 and 3,636,816, which, while important inventions in their own right, were limited in certain respects.

The cost, the bulky nature of and the precision required in fabricating, assembling and repairing the valve parts of the mentioned prior art stools, including an elongated valve stem which ran the length of a ram tube comprise consequential restrictions which limited the use and acceptance of the prior art stools. Inadequate precision in valve parts sometimes initially precipitated leakage of hydraulic fluid, as was sometimes also the case later due to misalignment of valve parts occasioned through wear, use and abuse, especially because the valve site was disposed substantially remote to the actuator and control portions of the stool. Shipping weight of the bulky valve parts is added to the cost problem.

BRIEF SUMMARY AND OBJECTS OF THE INVENTION

In brief summary, the present invention comprises improvements in medical stools and the like wherein a pressurized tank is located beneath the seat thereof and all valve parts, which extend and retract telescopically interrelated tubular members to change the height of the stool, are disposed substantially within a hollow center of the tank. The valve parts may be less precise, are relatively compact, weigh less, are more readily assembled and repaired and incur less inadvertent fluid leakage initially and following use. Moreover, the actuator and the controls of the improved stool are only a short distance from the valve parts per se, reducing the risk of misalignment, binding and sluggish responsiveness.

In addition a novel actuator, a unique seat/tank mounting arrangement and an improved connector for the stool base are provided.

With the foregoing in mind, it is a primary object of the present invention to provide improvements in medical stools and the like.

It is a further principal object of the present invention to provide a novel medical stool and the like wherein a pressurized tank is located beneath the seat of the stool and all valve parts, which extend and retract telescopically interrelated tubular members to change the height of the stool, are disposed substantially within a hollow center of the tank.

A further significant object of the present invention is the provision of a novel medical stool and the like wherein valve parts may be less precise, are relatively compact, weigh less, are more readily assembled and repaired, incur less inadvertent fluid leakage, and operate with substantial precision.

A further important object of the present invention is the provision of a novel medical stool and the like wherein the actuator and controls are disposed only a short distance from the valve parts reducing the risk misalignment, binding and sluggish responsiveness.

A further object of the present invention is the provision of a unique medical stool and the like having a novel actuator, a unique seat/tank mounting arrangement and/or an improved connector for the base thereof.

These and other objects and features of the present invention will be apparent from the detailed description taken with reference to the accompanying drawings.

BRIEF DESCRIPTION OF THE DRAWINGS

FIG. 1 is a side elevation of a stool embodying the present invention, the stool being shown in its elevated or extended position;

FIG. 2 is an enlarged fragmentary vertical cross section of the portion of the stool of FIG. 1 disposed beneath the seat thereof;

FIG. 3 is an enlarged vertical cross section of the valve assembly and actuator for the stool of FIG. 1;

DETAILED DESCRIPTION OF THE ILLUSTRATED EMBODIMENT

Figure 4:
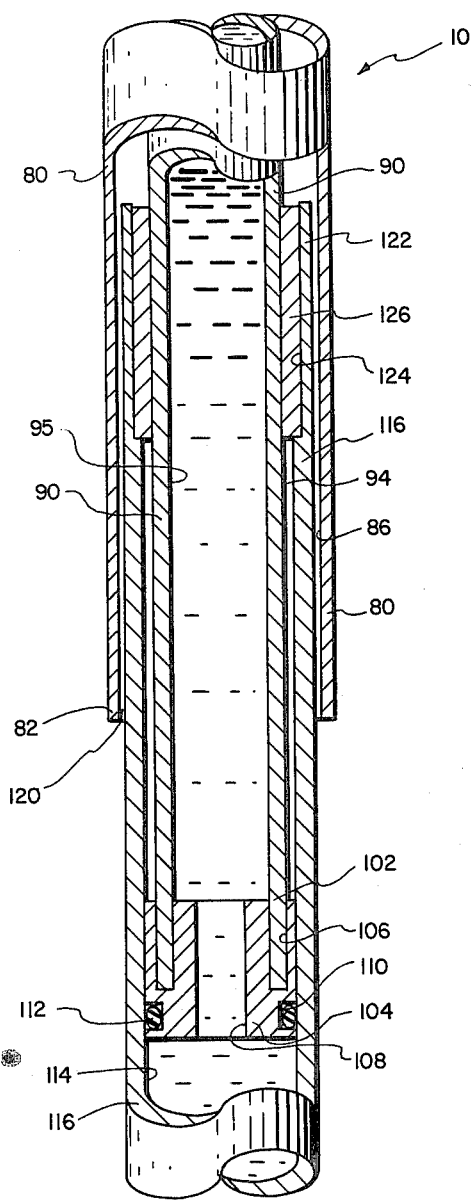
FIG. 4 is an enlarged fragmentary vertical cross section of the central portion of the stool of FIG. 1.
Figure 5:
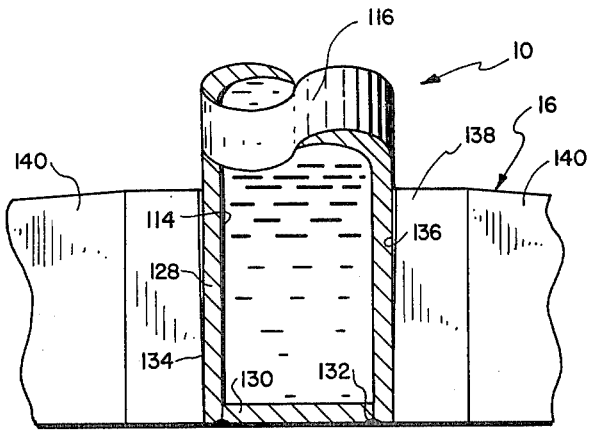
FIG. 5 is an enlarged fragmentary vertical cross section of the lower portion of the stool of FIG. 1 illustrating the manner in which the base of the stool supports the remainder thereof.

Reference is now made to the Figures wherein like numerals are used to designate like parts throughout. More specifically, a stool, generally designated 10, embodying the present invention, is illustrated in the Figures. The stool 10 comprises a seat 12 on the upper end of a vertical post assembly 14 which in turn is carried upon a base 16. The base 16 has floor engaging casters 18. Thus, the stool 10 is supported in an erect position for displacement along the floor through rotation of the caster in response to manually applied force. The seat 12 may be manipulated between an elevated position shown in solid lines in FIG. 1 and a lowered or retracted position shown in dotted lines in FIG. 1, as hereinafter more fully explained.

While any one of a large number of seats could be utilized, seat 12 is illustrated as comprising an interior cushion 20, a cover 22 and a generally flat or planar wood base or seat mounting plate 24. A plurality of stepped vertically directed apertures 26 are disposed in the mounting plate 24 at spaced locations along a common radius having the same center as the post assembly 14.

The upper end of the post assembly 14 carries an inverted bulbous funnel shaped tank 30 comprising a downwardly tapered curvilinear side wall 32 preferably formed of mild steel or the like, which terminates in a stepped lower end defining spaced radial shoulders 34 and 36 as well as annular wall portions 38 and 40. The annular wall portion 40 defines a bottom annular opening 42.

The tank 30 further comprises a top plate 44 welded or otherwise suitably secured at annular site 46 to the interior surface of the side wall 32. The top plate 44 further comprises an upwardly directed central flange 48 defining an annular opening 50. The tank further comprises an annular curvilinear mounting flange or skirt 52 which constitutes an upward extension of the side wall 32 and terminates in a horizontally directed lip 54. Lip 54 defines an array of apertures 56 located along a common radius. A screw 58 passes through each aperture 56 and each aligned stepped bore 26 in the seat mounting plate 24 and is secured in the indicated position by a stepped pressure nut 60, as is best illustrated in FIG. 2.

When the tank 30 is fabricated as indicated and installed as illustrated and as yet to be further explained, a hollow hermetically sealed reservoir 62 is provided which has hydraulicfluid disposed in the lower portion thereof and gas, such as air, under pressure disposed in the top portion thereof, for purposes hereinafter more fully explained.

The mounting flange or skirt 52 of the tank 30 further comprises an elongated slot 64 through which the distal end or handle 66 of an actuating lever 68 projects for manual manipulation as later more fully described.

The post assembly 14 comprises an exposed relatively thin wall cover sleeve 80, preferably fabricated from mild steel, which comprises a free lower end 82 and an attached upper end 84. The interior wall 86 of the cover sleeve 80 has a diameter substantially equal to the diameter of the tank annulus 38. End 84 of sleeve 80 is telescopically displaced along annulus 38 until the illustrated super position is achieved. Thereafter, the end 84 is secured to the tank wall 32 along an annular site 88, preferably by welding.

The post assembly 14 further comprises a ram tube 90, preferably formed of mild steel. Ram tube 90 extends concentrically through the reservoir 62 of the tank 30, with the top end 92 being exposed adjacent the tank top 44. The exterior wall surface 94 of the ram tube 90 has an outside diameter substantially the same as both the inside diameter 42 of tank annulus 40 and the inside diameter 50 of the vertical flange 48 at the top of the tank 30. The annulus 40 and the flange 48 are connected in an air tight fashion to the adjacent exterior surface 94 of the tube 90 along annular sites 96 and 98, respectively, as by welding or the like.

The ram tube 90 comprises two opposed, radially directed orifices 100 disposed therein at the upper end of the tube 90 which orifices are respectively disposed in fluid communication with the interior reservoir 62 of the tank 30 for purposes later to be more fully described.

As can be seen by observation of FIGS. 2-4, the longitudinal axis of the ram tube 90 is common with the longitudinal axis of the sleeve 80, but has a substantially longer axial length. The tube 90 comprises a lower end 102 to which is secured a bottom bearing 104. Bearing 104 provides an upward opening annular blind groove 106 into which the tube end 102 extends and is secured by use of a satisfactory bonding agent or the like. The bottom bearing 104 defines a relatively large axial passageway 108, the diameter of which is less than the interior diameter of the tube 90. Bottom bearing 104 further defines an annular groove 110 into which a seal 112 is placed for contiguous static and dynamic frictional engagement with the interior surface 114 of a lower tube 116 whereby fluid leakage between tubes 90 and 116 is substantially eliminated. Tube 116 is preferably fabricated of mild steel. The outside diameter of the bearing 104 is substantially the same as the inside diameter at surface 114 of the lower tube 116 so that the seal 112 is caused to wipe the tube surface 114 during relative downward displacement of tubes 90 and 116, as hereinafter described.

It should be noticed that the diameter of the inside surface 86 of the cover sleeve 80 is substantially larger than the outside diameter of the lower tube 116 so that an annular space 120 exists between sleeve 80 and tube 116 at all times. Thus, sleeve 80 is cosmetic.

The upper end 122 of the lower tube 116 comprises a stepped inside recess 124 into which a sleeve bearing 126 is press-fit. Bearing 126 has an inside diameter which causes the bearing 126 to be snugly contiguous with the outside surface 94 of the ram tube 90 to accommodate aligned relative reciprocation of the tubes 90 and 116. As can be appreciated by observance of the extended and retracted positions of the stool as illustrated in FIG. 1, at all times the tubes 90 and 116 telescopically overlap, more in the retracted position and less in the extended position.

The inside diameter defined by interior surface 114 of lower tube 116 is constant throughout the length of the lower tube 116. The lower end 128 thereof is closed by an end plug 130, which snugly fits to the surface 114 and is secured in the illustrated position by an annular weld or the like at site 132. Preferably, the exterior surface 134 at end 128 of tube 116 has a slight taper, on the order of 1°-2° so that it may be manually forced into and removed from a central opening 136 in the stool base 16.

The opening 136, which may be circular or tapered similar to the exterior surface 134, is defined by a central boss 138, with the base 16 being otherwise standard and conventional, comprising radial spokes 140 having caster-receiving blind bores or receptacles 142 at the distal ends thereof. Each caster receptacle 142 pivotally receives a conventional caster 18 having a wheel 144. Thus, the base 16 provides for readily releasably receiving the post assembly 14 in a rapid fashion and further provides adequate stability for maintaining the stool in its erect orientation both in the extended and retracted positions while providing the requisite mobility for rolling the stool along a floor from place to place as desired. Disassembly of the base 16 from the remainder may be rapidly and facilely manually achieved. The base 16 preferably is fabricated of mild steel.

Significantly, a valve assembly, generally designated 150 is concentrically disposed within the upper end of the ram tube 90. The overal length of the valve assembly 150 is substantially the same as the vertical axial distance spanned by the tank 30, resulting in a more precise operation at a significant reduction in cost when compared with prior art proposals.

More specifically, the valve assembly 150 comprises a valve sleeve housing 152 which is sized and shaped so as to be tightly retained in force-fit relation within the upper end of the ram tube 90 as illustrated. Valve sleeve 152 is preferably formed of steel and comprises an upper end 153, which is contiguously engaged by a retainer or snap ring 154. Retainer ring 154 is force-fit into an annular groove 156 exposed along the interior surface 95 adjacent the end 92 of the tube 90.

The upper end 153 of the valve sleeve 152 is stepped along the interior surface at site 160. Thus, a shoulder 162 is provided which constitutes an abutment against which compression spring 164 rests.

The interior annular surface 166 of the central portion of the valve sleeve 152 is of constant diameter but is enlarged at the lower end 168 to form stepped annular surfaces 170 and 172, respectively. Accordingly, valve seat shoulders 174 and 176, respectively, are provided.

The exterior annular surface 180 of the valve sleeve 152 is interrupted by four annular grooves identified as 182, 184, 186 and 188, from top to bottom. Grooves 182, 184 and 188 each receive an O-ring seal to thereby create a static seal, in each case, with the interior surface 95 of the ram tube 90. Annular groove 186 is radially aligned with the orifices 100 disposed in the tube 90 to accommodate displacement of hydraulic fluid. The annular groove 186 is in fluid communication with a plurality of radial passageways 190 disposed in the sleeve 152. Thus, hydraulic fluid may be caused to be displaced between the interior 166 of the valve sleeve 152 and the tank reservoir 62 via orifices 100, annular groove 186 and radial passageways 190.

The interior annular surface 172 of the valve sleeve 152 is provided with a radially disposed groove 192 into which is force-fit a retainer or snap ring 194. The retainer ring 194 holds a radially directed disc-shaped floating check valve 196 between the ring 194 and the seat shoulder 176. The diameter of the valve 196 is sized to be slightly less than the inside diameter of the annular surface 172 so that when the valve plate 196 is spaced from the shoulder 176, flow of hydraulic fluid around the perimeter thereof may occur. However, when the plate check valve 196 is caused to be seated against the shoulder 176, hydraulic fluid may flow only through a small central port 197 therein.

A relatively short, small diameter valve shaft 200 is snugly, though reciprocably disposed concentrically within the valve sleeve 152. Accordingly, the diameter of the main body of the shaft 200 is only slightly smaller than the inside diameter of the surface 166 of the valve sleeve 152. The outside surface 202 of the valve shaft 200 is centrally interrupted by a pair of annular grooves 204 and 206, each of which contain an O-ring seal to create both static and dynamic seals with the interior surface 166 of the static valve sleeve 152. Thus, hydraulic fluid is substantially prevented from migrating upward between the shaft 200 and the sleeve 152.

The shaft 200 is necked down near its lower end to provide a reduced diameter portion 205, which defines an annular chamber 207 aligned and in fluid communication with the radial passageways 190, previously described.

The lower end of the shaft 200 comprises a valve head 210, which is sized and shaped so as to seat against the sleeve shoulder 174 when the valve shaft 200 is in its most elevated position, and to be spaced from the shoulder 174 and adjacent annular surface 170 when the shaft 200 is displaced downward from its most elevated position. The latter position accommodates flow of hydraulic fluid around the valve head 210.

The exterior surface 202 of the shaft 200 at the upper end 212 thereof is interrupted by a radially disposed annular groove 214 into which a snap or retainer ring 216 is force-fit. The previously mentioned compression spring 164 is sized and shaped so that the upper end thereof abuts against the retainer ring 216 so as to shorten the unstressed axial length of the spring, leaving the spring to exert a compressive force between the shoulder abutment 162 and the retainer ring 216. This compressive force urges the shaft 200 into its most elevated position thereby causing the valve head 210 to normally seat against the sleeve shoulder 174.

The seat mounting plate 24 is provided with a central recess 220 sized and shaped to receive a thin pressure plate 222 therein in flush relationship. The plate 222 is provided with a plurality of apertures 224 through which wood screws 226 pass. The screws 226 are threadedly secured in the seat base 224.

The plate 222 is also provided with an eccentric aperture 230. A pop rivet 232 projects through and is secured against inadvertent removal adjacent the aperture 230. The pop rivet 232 also passes through an aligned aperture 234 in elongated angular actuator 68 at or adjacent to the angle site. The actuator 68 is constructed so as to comprise a top rigid metal plate 236, which, in the absence of stress, is flush and contiguous with the lower surface of the plate 222 directly above the valve assembly 150. The projecting handle 66 of the actuator 68 is disposed at a slight angle, preferably on the order of 15°, in respect to that portion of the plate 266 normally contiguous with the plate 222. Thus, the pop rivet 232 constitutes a fulcrum about which the actuator may be caused to rock rivet 232 also fastens the actuator to the plate 222.

The actuator 68 is recessed at site 238 so that the top 212 of the valve shaft 200 has a slight clearance in respect to the bottom surface of the actuator plate 236. Accordingly, when the exposed ends 66 of the actuator 68 is manually lifted from beneath the seat, the fulcrum at pop rivet 232 accommodates a pivotal action such that the portion of the plate 236 adjacent the top 212 of the valve shaft 200 moves downward, which in turn displaces the valve shaft 200 downward whereby the valve head 210 becomes spaced from the shoulder 174 to accommodate hydraulic fluid flow.

In the fully extended position as illustrated in the Figures (with the exception of the dotted line representation shown in FIG. 1), hydraulic fluid or the like is contained within the lower portion of the tank 30. This level is indicated by the numeral 250. However, it is to be appreciated that the fluid level 250 may vary in its location, depending upon the shape and sizes of the various parts used to form the stool, but, in the extended position, must be at an elevation above the orifices 100 in the ram tube 90. That portion of the tank reservoir 62 above the hydraulic fluid level 250 contains air under pressure, introduced in any conventional way, the pressure of which is greater than atmospheric pressure but less in total force than the weight of the user of the stool. Thus, hydraulic fluid or the like, when the stool is in its vertically erect and fully extended position is contained within the lower region of the tank 32 and within the orifices 100, the annular groove 186, the passageways 190, the chamber 207, the space between the valve head 210 and the disc shaped check valve 196, all of the interior of the ram tube 90 below the check valve 196 and that portion of the lower tube 116 below the bottom bearing 104.

When the user desires to lower the stool from its fully extended postion to its fully retracted position or to any position intermediate the fully extended and fully lowered position, the user causes his or her weight to be placed upon the seat 12 and elevates the handle 66 of the actuator 68, which lowers the valve shaft 200 to accommodate flow of hydraulic fluid across the valve head 210. This flow is in an upward direction with the central aperture 197 of the disc valve 196 restricting the rate of flow to thereby control the rate at which the seat 12 is lowered. Thus, the ram tube 90 is telescopically lowered into the tube 116. The foregoing action is accomplished by reason of the fact that the total force of the compressed air within the tank reservoir 62 (direct counter to the weight force) is of less magnitude than the weight of the user. When a desired seat location is attained, the user merely releases the handle 66 of the actuator 68 and the spring 164 returns both the actuator 68 and the valve shaft 200 to their respective at rest positions. This causes the valve head 210 to once more seat against the shoulder 174 thereby terminating further flow of hydraulic fluid across the valve head 210.

When the stool 10 is in a position other than its fully extended position and it is desired to elevate the seat 12, the operator removes his or her weight from the seat 12, lifts upon the handle 66 of the actuator 68, which causes the valve head 210 to be displaced downward away from the shoulder 174. Air pressure within the tank causes flow of hydraulic fluid across the valve head 210. This hydraulic flow is in a downward direction and occurs not only through the central port 197 but around the perimeter of the disc-shaped check valve 196. This flow causes the ram tube 90 to telescopically elevate upward in respect to the lower tube 116 thereby extending the effective length of the post assembly 14 and the overall length of the stool 10. When the seat has reached the elevation desired by the user, the actuator 68 is released, which causes the valve head 210 to once more seat against the shoulder 174 thereby terminating further flow of hydraulic fluid across the valve head 210.

It should be readily apparent that, when the actuator 68 is in its at rest position, the existing position of the stool 10 is retained.

The invention may be embodied in other specific forms without departing from the spirit or essential characteristics thereof. The present embodiment is therefore considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A medical stool and the like having a selectively variable effective length, the stool comprising:
   top seat means;
   bottom base means;
   intermediate generally hollow post means, pressurizing tank means, valve means and control means;
   the tank means comprising mounting means for joining the tank means to the seat means, an interior hermetically sealed generally annular reservoir containing liquid in the bottom for selective communication to and from the hollow interior of the post means across the valve means and gas under pressure above the liquid, the tank means further comprising a hollow center external of the tank reservoir;
   the control means by which the valve is controlled comprising a manual actuator at least partially disposed directly beneath the seat means;
   the post means comprising hollow ram tubular means and hollow cylinder tubular means, the two tubular means having juxtaposed ends telescopically reciprocably interconnected, the other end of one of the tubular means being connected in loadtransferring relation to the tank means, the other end of the other tubular means being connected in load transferring relation to the base means, the hollow interior of the two tubular means being in substantially open and unrestricted fluid communication one with the other to thereby form a composite variable volume liquid reservoir;
   the valve means being disposed substantially entirely within the hollow of the tank means and comprising valve shaft means urged by bias means away from an open position to a closed position and stationary elongated sleeve means having liquid flow path means extending between the tank reservoir and the valve shaft means, which valve shaft means are reciprocably disposed within the sleeve means, the valve shaft means comprising valve head means normally engaging valve seat means and recess means accommodating liquid flow across the valve head means and along the flow path means between the tank reservoir and the variable volume reservoir to selectively elevate and lower the seat by changing the effective length of the post means.

2. A medical stool or the like according to claim 1 wherein the seat means comprises bottom mounting base means and wherein the mounting means of the tank means comprise flange means contiguous with the mounting base means and further comprising means fastening the flange means to the mounting base means in flush relationship.

3. A medical stool and the like according to claim 2 further comprising slot means in the flange means through which the actuator displaceably extends to expose a cantilevered free end, the actuator comprising a generally radially extending lever pivotally mounted at a fulcrum site at the bottom mounting base means, the other end of the lever actuator being in force-applying relation to the upper end of the valve shaft means so that manual rocking of the lever above the fulcrum site opens the valve means by displacing the valve shaft means to unseat the valve head means counter to the force of the bias means.

4. A medical stool and the like according to claim 1 further comprising an exterior sleeve attached to and depending from the lower portion of the tank means a distance greater than the axial length of the one tubular means to loosely encase and conceal at all time the one tubular means and the telescopic overlap between the two tubular means.

5. A medical stool and the like according to claim 1 wherein the tank means comprise a central tubular wall defining the hollow center and an outside wall lapped at the bottom thereof upon and rigidly fastened to the one tubular means.

6. A medical stool and the like according to claim 5 wherein the central tubular wall comprises an upwardly directed extension of the one tubular means.

7. A medical stool and the like according to claim 1 wherein the bias means comprise a spring compressively interposed between a first abutment site carried near the upper end of the valve shaft means and a second abutment site carried by the stationary sleeve means near the top thereof.

8. A medical stool and the like according to claim 1 wherein the valve means further comprise a disc-shaped flow control valve reciprocably disposed between a second valve seat means and stop means within the path of the liquid between the valve head means and the variable volume reservoir, the flow control valve accommodating a limited rate of fluid flow through aperture means therein when the flow control valve is seated against the second valve seat and accommodating liquid flow around the perimeter of the flow control valve when the flow control valve is unseated from the second valve seat means.

9. A medical stool and the like according to claim 1 wherein the sleeve means of the valve means are force fit into the hollow interior of the upper end of the one tubular means which upper end centrally extend substantially through the tank means.

10. A medical stool and the like according to claim 9 wherein the upper end of the one tubular means also comprises interior wall means of the tank means.

11. A medical stool and the like according to claim 1 wherein the other end of the other tubular means is closed and securely force fit connected into an opening in the base means.

12. A power unit for a medical stool and the like having a selectively variable length, the power unit comprising:

generally hollow post means, pressurizing tank means and valve means;

the tank means comprising an interior hermetically sealed generally annular reservoir containing liquid in the bottom for selective communication to and from the hollow interior of the post means across the valve means and gas under pressure above the liquid, the tank means further comprising a hollow center external of the tank reservoir;

the post means comprising hollow ram tubular means and hollow cylinder tubular means, the two tubular means having juxtaposed ends telescopically reciprocably interconnected, the other end of the one tubular means being connected to the tank means, the other end of the other tubular means comprising a fluid tight closure, the hollow interior of the two tubular means being in substantial open and unrestricted fluid communication to thereby form a composite variable volume elongated liquid reservoir, the axial length of which is always substantially greater than the axial length of the tank means;

the valve means being disposed substantially entirely within the hollow of the tank means and comprising valve shaft means urged by bias means away from an open position to a closed position and stationary elongated sleeve means having liquid flow path defining means extending between the tank reservoir and the valve shaft means which valve shaft means are reciprocably disposed within the sleeve means, the valve shaft means comprising valve head means normally engaging valve seat means and recess means adjacent the valve head means accommodating liquid flow across the valve shaft means and along the flow path means between the tank reservoir and the variable volume reservoir to selectively change the effective length of the post means.

* * * * *